(12) United States Patent
Purcell et al.

(10) Patent No.: US 8,298,265 B2
(45) Date of Patent: *Oct. 30, 2012

(54) VARIABLE ANGLE SPINAL SCREW ASSEMBLY

(76) Inventors: Thomas Purcell, Solana Beach, CA (US); Don Hair, Moreno Valley, CA (US); Tamas T. Frech, Sun City, CA (US)

(*) Notice: Subject to any disclaimer, the term of this patent is extended or adjusted under 35 U.S.C. 154(b) by 1095 days.

This patent is subject to a terminal disclaimer.

(21) Appl. No.: 12/154,448

(22) Filed: May 23, 2008

(65) Prior Publication Data

US 2008/0243189 A1    Oct. 2, 2008

Related U.S. Application Data

(63) Continuation of application No. 10/848,946, filed on May 19, 2004, now Pat. No. 7,377,923.

(60) Provisional application No. 60/472,578, filed on May 22, 2003, provisional application No. 60/527,060, filed on Dec. 4, 2003.

(51) Int. Cl.
*A61B 17/70* (2006.01)
(52) U.S. Cl. ..................................................... 606/246
(58) Field of Classification Search .................. 606/246, 606/264–272, 301, 305, 308, 328; 403/76, 403/362; 411/393
See application file for complete search history.

(56) References Cited

U.S. PATENT DOCUMENTS

| | | |
|---|---|---|
| 4,805,602 A | 2/1989 | Puno et al. |
| 4,946,458 A | 8/1990 | Harms et al. |
| 5,176,680 A | 1/1993 | Vignaud et al. |
| 5,207,678 A | 5/1993 | Harms et al. |
| 5,217,497 A | 6/1993 | Mehdian |
| 5,360,431 A | 11/1994 | Puno et al. |
| 5,443,467 A | 8/1995 | Biedermann et al. |
| 5,466,237 A | 11/1995 | Byrd, III et al. |
| 5,520,689 A | 5/1996 | Schlapfer et al. |
| 5,520,690 A | 5/1996 | Errico et al. |
| 5,549,608 A | 8/1996 | Errico et al. |
| 5,578,034 A | 11/1996 | Estes |
| 5,586,984 A | 12/1996 | Errico et al. |
| 5,607,426 A | 3/1997 | Ralph et al. |
| 5,647,873 A | 7/1997 | Errico et al. |
| 5,669,911 A | 9/1997 | Errico et al. |
| 5,683,392 A | 11/1997 | Richelsoph et al. |

(Continued)

FOREIGN PATENT DOCUMENTS

DE          29903342          6/1999

(Continued)

*Primary Examiner* — Alvin Stewart
*Assistant Examiner* — David Comstock
(74) *Attorney, Agent, or Firm* — John C. McMahon

(57) ABSTRACT

A spinal screw assembly providing an adjustable securement of a fixation rod across at least two vertebrae. The assembly includes a pedicle screw having a spherical head portion, a threaded shaft portion and a tool engagement surface in the head portion for use in driving the screw into a vertebrae. The head portion of the screw is positioned in a body member adjacent a curvilinear surface disposed about an aperture in the end of the body member such that the shaft portion of the screw extends therethrough and the curvilinear inner surface abuts and mates with the head portion of the screw so as to define a ball joint therewith. The body member additionally defines a pair of opposed parallel slots therein adapted to receive a portion of the fixation rod and a locking cap bears against the fixation rod to releasably secure the rod within the assembly.

24 Claims, 14 Drawing Sheets

U.S. PATENT DOCUMENTS

| | | |
|---|---|---|
| 5,690,630 A | 11/1997 | Errico et al. |
| 5,720,751 A | 2/1998 | Jackson |
| 5,725,528 A | 3/1998 | Errico et al. |
| 5,728,098 A | 3/1998 | Sherman et al. |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,879,350 A | 3/1999 | Sherman et al. |
| 5,888,204 A | 3/1999 | Ralph et al. |
| 5,891,145 A | 4/1999 | Morrison et al. |
| 5,954,725 A | 9/1999 | Sherman et al. |
| 5,964,760 A | 10/1999 | Richelsoph |
| 6,004,322 A | 12/1999 | Bernstein |
| 6,053,917 A | 4/2000 | Sherman et al. |
| 6,083,224 A | 7/2000 | Gertzbein et al. |
| 6,132,434 A | 10/2000 | Sherman et al. |
| 6,146,383 A | 11/2000 | Studer et al. |
| 6,248,105 B1 | 6/2001 | Schlapfer et al. |
| 6,287,311 B1 | 9/2001 | Sherman et al. |
| 6,296,642 B1 | 10/2001 | Morrison et al. |
| 6,309,390 B1 | 10/2001 | Le Couedic et al. |
| 6,328,739 B1 | 12/2001 | Liu et al. |
| RE37,665 E | 4/2002 | Ralph et al. |
| 6,368,321 B1 | 4/2002 | Jackson |
| 6,454,773 B1 | 9/2002 | Sherman et al. |
| 6,485,491 B1 | 11/2002 | Farris et al. |
| 6,488,681 B2 | 12/2002 | Martin et al. |
| 6,520,963 B1 | 2/2003 | McKinley |
| 6,623,485 B2 | 9/2003 | Doubler et al. |
| 6,641,586 B2 | 11/2003 | Varieur |
| 6,660,004 B2 | 12/2003 | Barker et al. |
| 6,716,214 B1 | 4/2004 | Jackson |
| 6,733,502 B2 | 5/2004 | Altarac et al. |
| 6,755,829 B1 | 6/2004 | Bono et al. |
| 6,802,844 B2 | 10/2004 | Ferree |
| 6,843,791 B2 | 1/2005 | Serhan |
| 6,893,443 B2 | 5/2005 | Frigg et al. |
| 6,964,666 B2 | 11/2005 | Jackson |
| 6,981,973 B2 | 1/2006 | McKinley |
| 7,022,122 B2 | 4/2006 | Amrein et al. |
| RE39,089 E | 5/2006 | Ralph et al. |
| 7,087,057 B2 | 8/2006 | Konieczynski et al. |
| 7,163,539 B2 | 1/2007 | Abdelgany et al. |
| 7,166,108 B2 | 1/2007 | Mazda et al. |
| 7,291,153 B2 | 11/2007 | Glascott |
| 7,377,923 B2 * | 5/2008 | Purcell et al. ............. 606/248 |
| 7,686,834 B2 | 3/2010 | Saint Martin |
| 2002/0026193 A1 | 2/2002 | Barker et al. |
| 2002/0120272 A1 | 8/2002 | Yuan et al. |
| 2002/0161370 A1 | 10/2002 | Frigg et al. |
| 2003/0004511 A1 | 1/2003 | Ferree |
| 2003/0055426 A1 | 3/2003 | Carbone et al. |
| 2003/0125741 A1 | 7/2003 | Biedermann et al. |
| 2004/0039384 A1 | 2/2004 | Boehm, Jr. et al. |
| 2004/0097933 A1 | 5/2004 | Lourdel et al. |
| 2004/0111088 A1 | 6/2004 | Picetti et al. |
| 2004/0147929 A1 | 7/2004 | Biedermann et al. |
| 2004/0153068 A1 | 8/2004 | Janowski et al. |
| 2004/0158247 A1 | 8/2004 | Sitiso et al. |
| 2004/0181224 A1 | 9/2004 | Biedermann et al. |
| 2004/0186473 A1 | 9/2004 | Cournoyer et al. |
| 2005/0038432 A1 | 2/2005 | Shaolian et al. |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0080420 A1 | 4/2005 | Farris et al. |
| 2005/0085813 A1 | 4/2005 | Spitler et al. |
| 2005/0154390 A1 | 7/2005 | Biedermann et al. |
| 2005/0159750 A1 | 7/2005 | Doherty |
| 2005/0182410 A1 | 8/2005 | Jackson |
| 2005/0187548 A1 | 8/2005 | Butler et al. |
| 2005/0203516 A1 | 9/2005 | Biedermann et al. |
| 2005/0216000 A1 | 9/2005 | Colleran et al. |
| 2005/0222570 A1 | 10/2005 | Jackson |
| 2005/0228379 A1 | 10/2005 | Jackson |
| 2005/0228385 A1 | 10/2005 | Iott et al. |
| 2005/0261687 A1 | 11/2005 | Garamszegi et al. |
| 2005/0283244 A1 | 12/2005 | Gordon et al. |
| 2006/0004357 A1 | 1/2006 | Lee et al. |
| 2006/0095038 A1 | 5/2006 | Jackson |
| 2006/0111715 A1 | 5/2006 | Jackson |
| 2006/0142761 A1 | 6/2006 | Landry et al. |
| 2006/0200128 A1 | 9/2006 | Mueller |
| 2006/0247636 A1 | 11/2006 | Yuan et al. |
| 2006/0264962 A1 | 11/2006 | Chin et al. |
| 2006/0276791 A1 | 12/2006 | Shluzas |
| 2006/0293659 A1 | 12/2006 | Alvarez |
| 2006/0293665 A1 | 12/2006 | Shluzas |
| 2007/0016200 A1 | 1/2007 | Jackson |
| 2007/0093831 A1 | 4/2007 | Abdelgany et al. |
| 2007/0093832 A1 | 4/2007 | Abdelgany |

FOREIGN PATENT DOCUMENTS

| | | |
|---|---|---|
| EP | 0572790 | 12/1993 |
| EP | 0885598 | 12/1998 |
| EP | 0951245 | 10/1999 |
| EP | 0954247 | 11/1999 |
| EP | 1090595 | 4/2001 |
| EP | 1121902 | 8/2001 |
| EP | 1248573 | 10/2002 |
| WO | WO91/16020 | 10/1992 |
| WO | WO98/12976 | 4/1998 |
| WO | WO98/12977 | 4/1998 |
| WO | WO98/34554 | 8/1998 |
| WO | WO00/42930 | 7/2000 |
| WO | WO01/15612 | 3/2001 |
| WO | WO01/52758 | 7/2001 |
| WO | WO02/076315 | 10/2002 |
| WO | WO03/015648 | 2/2003 |
| WO | WO2004/017847 | 3/2004 |
| WO | WO2004/041100 | 5/2004 |
| WO | WO2005/018470 | 3/2005 |
| WO | WO2005/018471 | 3/2005 |
| WO | WO2005/065397 | 7/2005 |
| WO | WO2005/070165 | 8/2005 |
| WO | WO2005/012195 | 11/2005 |
| WO | WO2006/012088 | 2/2006 |

* cited by examiner

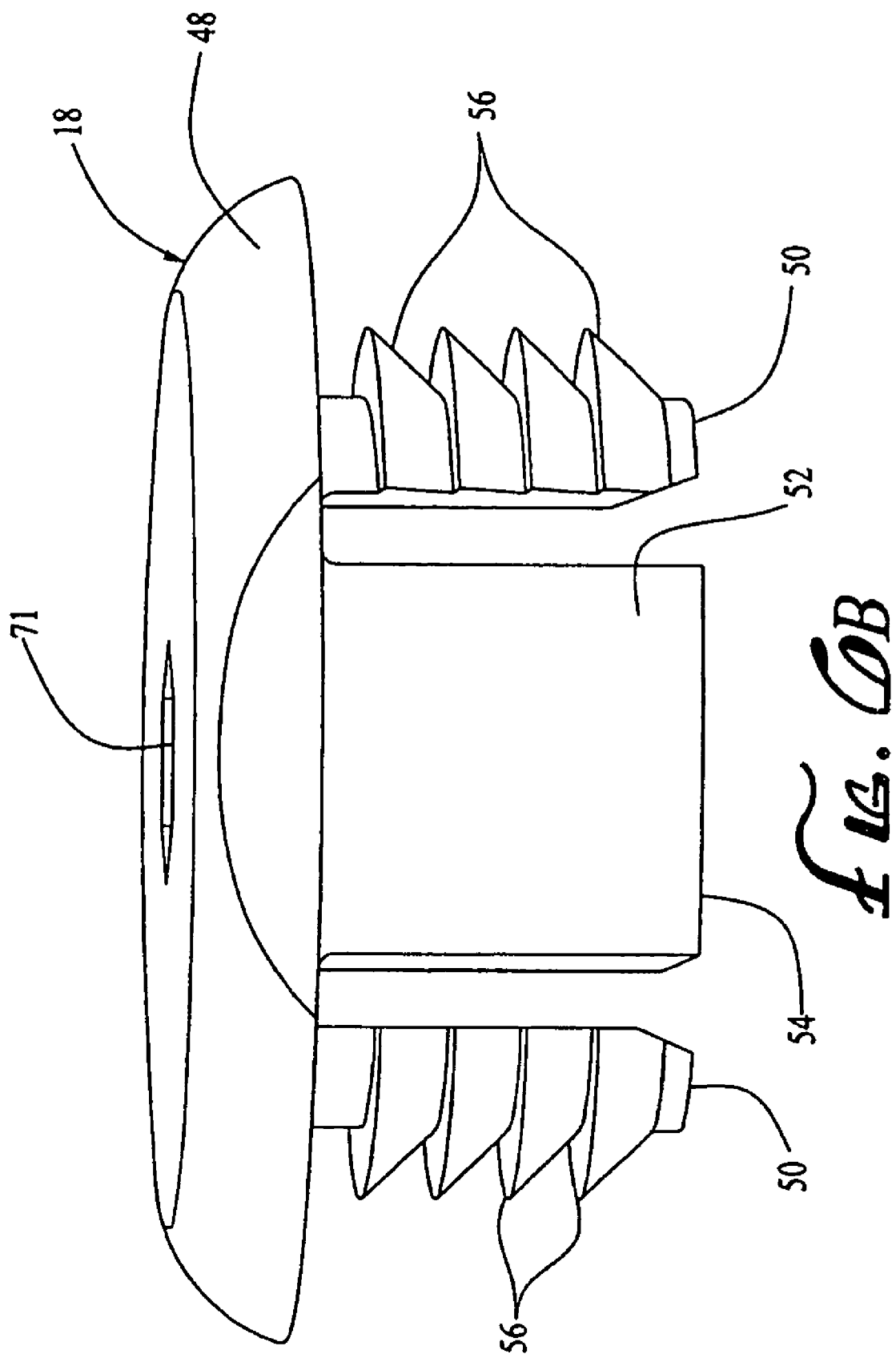

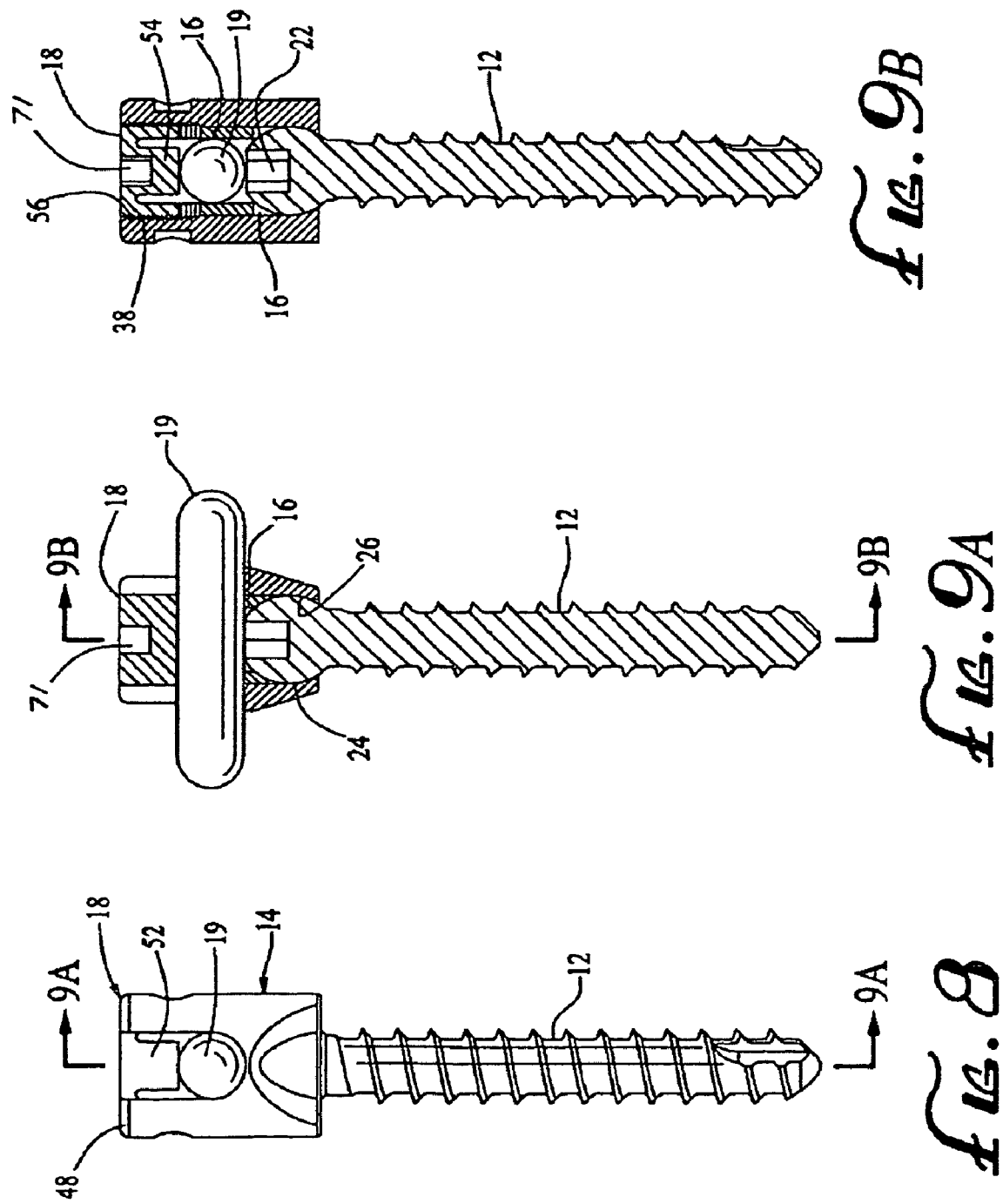

VARIABLE ANGLE SPINAL SCREW ASSEMBLY

CROSS-REFERENCE TO RELATED APPLICATIONS

This application is a continuation of U.S. patent application Ser. No. 10/848,946, filed May 19, 2004 that claims the benefit of U.S. Provisional Application No. 60/472,578, filed May 22, 2003 and U.S. Provisional Application No. 60/527,060, filed Dec. 4, 2003.

BACKGROUND OF THE INVENTION

The present invention relates generally to an apparatus for internal fixation of the spine and, more specifically to a novel locking mechanism for a variable angle spinal screw assembly that provides for easier implantation, a wide range of motion, ease of disassembly for adjustment or replacement of the stabilization rod and eliminates conventional threaded engagements and the crossover threading, torquing and other problems associated therewith.

Certain spinal conditions, including a fracture of a vertebra and a herniated disc, indicate treatment by spinal immobilization. Several methods of spinal joint immobilization are known, including surgical fusion and the attachment of pins and bone plates to the affected vertebras. One known device is a bone interface anchor inserted into at least two spaced-apart vertebras, with a stabilization rod interconnecting the two or more anchors to stabilize the vertebras spanned by the anchors. Specifically, a bone screw is received within a socket formed in the anchor. The anchor further includes a channel, extending perpendicular to the longitudinal axis of the bone screw, for receiving the stabilization rod. The anchor further comprises a threaded portion above the channel. After the bone screw and anchor have been inserted into the bone material, the rod is placed within the channel and a nut is mated with the external threads of the anchor. The nut applies a compressive force between the rod and the screw head to firmly fix the rod between the spanned vertebras and thus stabilize the spinal vertebrae.

During surgical implantation of these prior art stabilization systems, the surgical site is crowded with tissue masses, sponges and other surgical implements that obstruct access to the anchor threads. Given the difficult access, it is possible for the surgeon to cross-thread the nut with the threads of the anchor after the fixation rod is in place. If the threads of the anchor are cross-threaded, the cross-threaded coupling must be removed and replaced before the surgery can proceed. In addition, the threaded fastener (e.g., the nut) is frequently removed and then reinstalled as the surgeon makes progressive bends to contour the fixation rod. This increases the surgery with each on-off iteration and further increases the chances of cross-threading.

Another problem associated with threaded attachments is the torque exerted on the anchor during the tightening of the threaded fastener about the upper end portion of the fixation device. This torque can inadvertently introduce stress points along the rod, bend the rod or even loosen the threaded engagement of the anchor in the bone. The elimination of the conventional threaded attachments in the fixation device of the present invention also obviates these problems associated with torquing.

The angle at which the anchor screws extend from the vertebra pedicle is dictated by the spinal curvature, the orientation of individual vertebra within the spine, and the surgeon's placement of the screw within the pedicle. For example, there is considerable spinal curvature in the region of the S1-L5 vertebra junction and the angle between the longitudinal axis of the screws and the vertebra in that region vary over a wide range. Also, it may be necessary to displace one or more of the anchors from the spin midline to effectuate maximum spinal stabilization. Thus, the rod-receiving channels are typically not collinear nor coplanar and, the rod must be shaped or contoured by the surgeon during the implantation procedure to fit within the channels along the spinal column. The prior art systems allow the coupling unit to pivot with respect to the screw over a range of about .+-.20.degree. to .+-.30.degree., providing some margin for the surgeon to place the rod within the channel.

One challenge with current variable angle or polyaxial systems is aligning the coupling units in a manner that minimizes pre-insertion rod contouring while allowing the surgeon maximum range to optimize pedicle screw placement. This is especially challenging when fusing the S1-L5 junction. The prior art coupling units allow only a limited range of motion with respect to the screw head. The present invention allows a first range of motion in all directions, but also provides an extended range of motion in the medial-lateral-inferior direction (head-to-toe). This extended range of motion, as compared to the prior art, allows the surgeon additional freedom in locating the screws and eases the assembly process by reducing the requirement for rod contouring.

Thus, the present invention provides an extended range of motion as compared to the prior art, allowing the surgeon additional freedom in locating the screws and easing the assembly process by reducing the requirements for rod contouring. The present invention additionally eliminates the numerous problems heretofore experienced with threaded fasteners. The result is a significantly improved variable angle spinal screw assembly.

SUMMARY OF THE INVENTION

Briefly, the present invention comprises a variable angle spinal screw assembly for providing an adjustable securement of a stabilization rod between at least two spaced-apart vertebrae to effect internal fixation of the spine across the affected vertebrae. The assembly is used with at least one other such assembly to secure the fixation rod and includes a pedicle screw, a body member and a locking cap. The pedicle screw has a substantially spherical head portion defining a slot therein used to drive the screw into a vertebrae. The body member is generally cylindrical in configuration and is adapted to receive the head portion of the pedicle screw and cooperate therewith so as to define a modified ball joint to allow variable angular movement of the body member with respect to the pedicle screw with the threaded shaft portion of the screw extending through an opening in the inner end of the body member (or lower end as seen from the perspective shown in the drawings). The body member additionally defines a pair of opposed parallel slots axially disposed in the side wall thereof to receive a portion of the cylindrical fixation rod. The interior walls of the upper portion of the body member are provided with serrations defining a plurality of axially aligned ratchet teeth. The ratchet teeth are adapted to cooperate with opposed mating teeth formed on the outer surface of a locking cap such that upon pressing the locking cap downwardly within the body member of the assembly against the fixation rod and the rod against the head of the pedicle screw, the interlocking teeth will hold the cap in place and secure the fixation rod in place within the assembly. By rotating the locking cap with respect to the body member, the ratchet teeth are disengaged, relieving the pressure of the cap on the fixation rod and thus releasing the securement of the rod.

By providing the body member of the assembly with a rounded interior surface about the lower opening therein that mates with the rounded lower surface of the spherical screw head and with concave exterior surfaces on the underside of the body member about said opening, the angular orientation of the central axis of the body member relative to the pedicle screw is widely variable, providing an extended range of motion to facilitate surgical installation. Through the cooperation of the interlocking ratchet teeth on the body member and locking cap, installation is further facilitated and the disadvantages of conventional threaded fasteners are obviated.

In preferred embodiments of the present invention, a bushing is employed within the body member to better distribute the longitudinal forces exerted on the pedicle screw. The bushing can be of a generally cylindrical configuration, positioned adjacent the interior side wall of the body member and defines a seat for the fixation rod and a bifurcated depending skirt that abuts and mates with portions of the head of the pedicle screw upon being urged thereagainst by the locking cap pressing downwardly on the fixation rod. As a result, the force exerted on the screw is distributed about the head of the screw to improve the locking securement between the screw and the body member.

In addition, by providing a keyed interface between the pedicle screw head and the body member, the pedicle screw can be inserted into the bone by the surgeon unencumbered by the body member. The body member can then be aligned with the head of the embedded screw, slid onto and over the screw head, reoriented so as to mate the inner lower surface of the body member with the screw head to define the above-described modified ball joint and the resulting variable angle or polyaxial relationship. Such a keyed interface can be provided by a threaded engagement between the lower end of the body member and fixed screw head by which the body member can be screwed onto and over the head of the embedded screw. Alternatively, the screw head and body member opening can be multi-sided and configured so as to allow the body member to be slid over the screw head only when the two components are in a given alignment. Once the body member is slid over the head and rotated so as to misalign the respective sides, the body member is locked onto the screw head and the variable angle mating relationship therebetween is formed.

It is the principal object of the present invention to provide an improved securement of a fixation rod between two or more spaced-apart vertebrae to effect internal fixation of the spine across the affected vertebrae.

This and other objects and advantages of the present invention will be readily apparent from the following detailed description taken in conjunction with the accompanying drawings.

BRIEF DESCRIPTION OF THE DRAWINGS

FIGS. 6A and 6B are perspective views of a first embodiment of the cap of the present invention.

FIG. 8 is a side view of the variable angle spinal screw assembly of the present invention.

FIG. 9A is a sectional view taken along the line A-A of FIG. 8.

FIG. 9B is a sectional view taken along the line B-B of FIG. 8.

DETAILED DESCRIPTION OF THE PREFERRED EMBODIMENT

Figure 1:
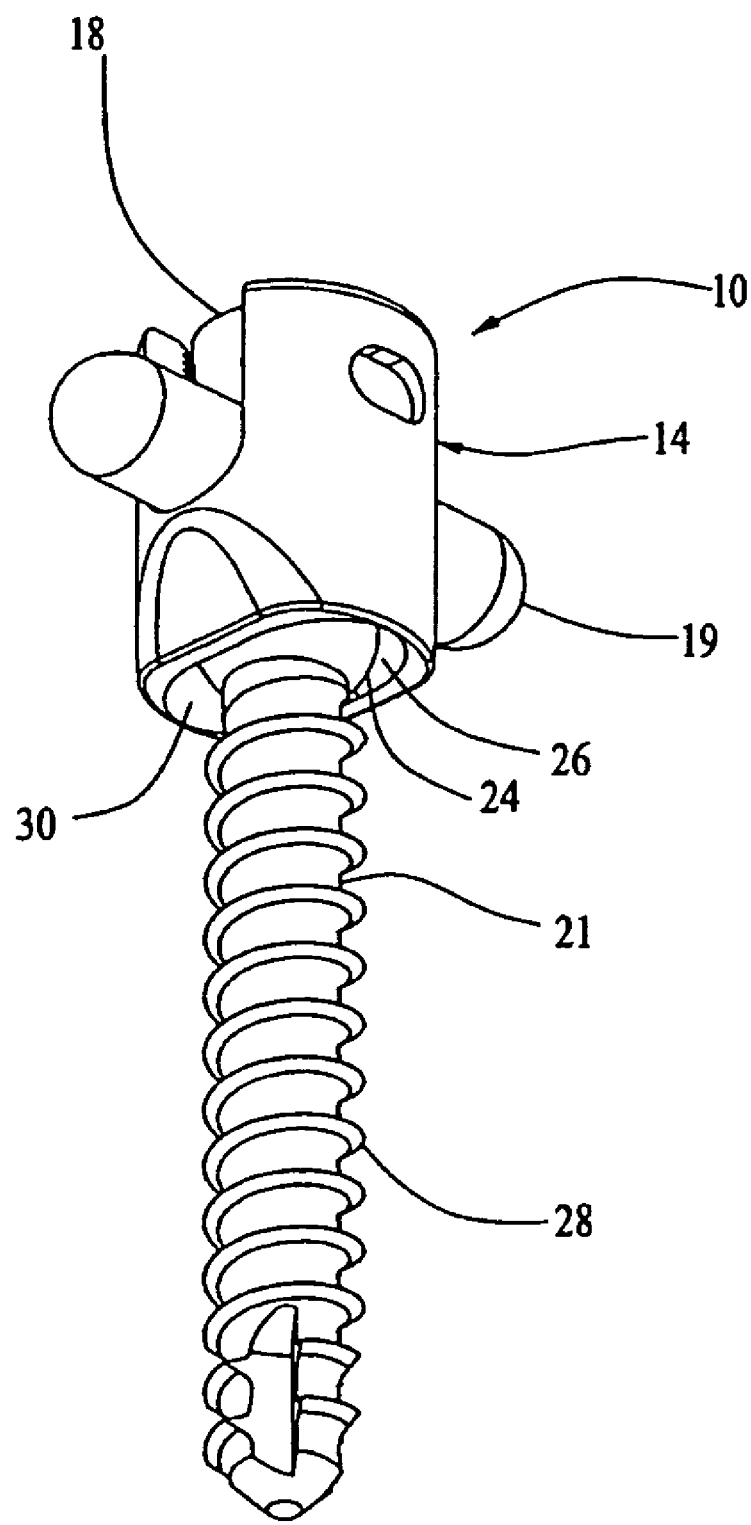
FIG. 1 is a perspective view of the variable angle spinal screw assembly of the present invention.
Figure 2:
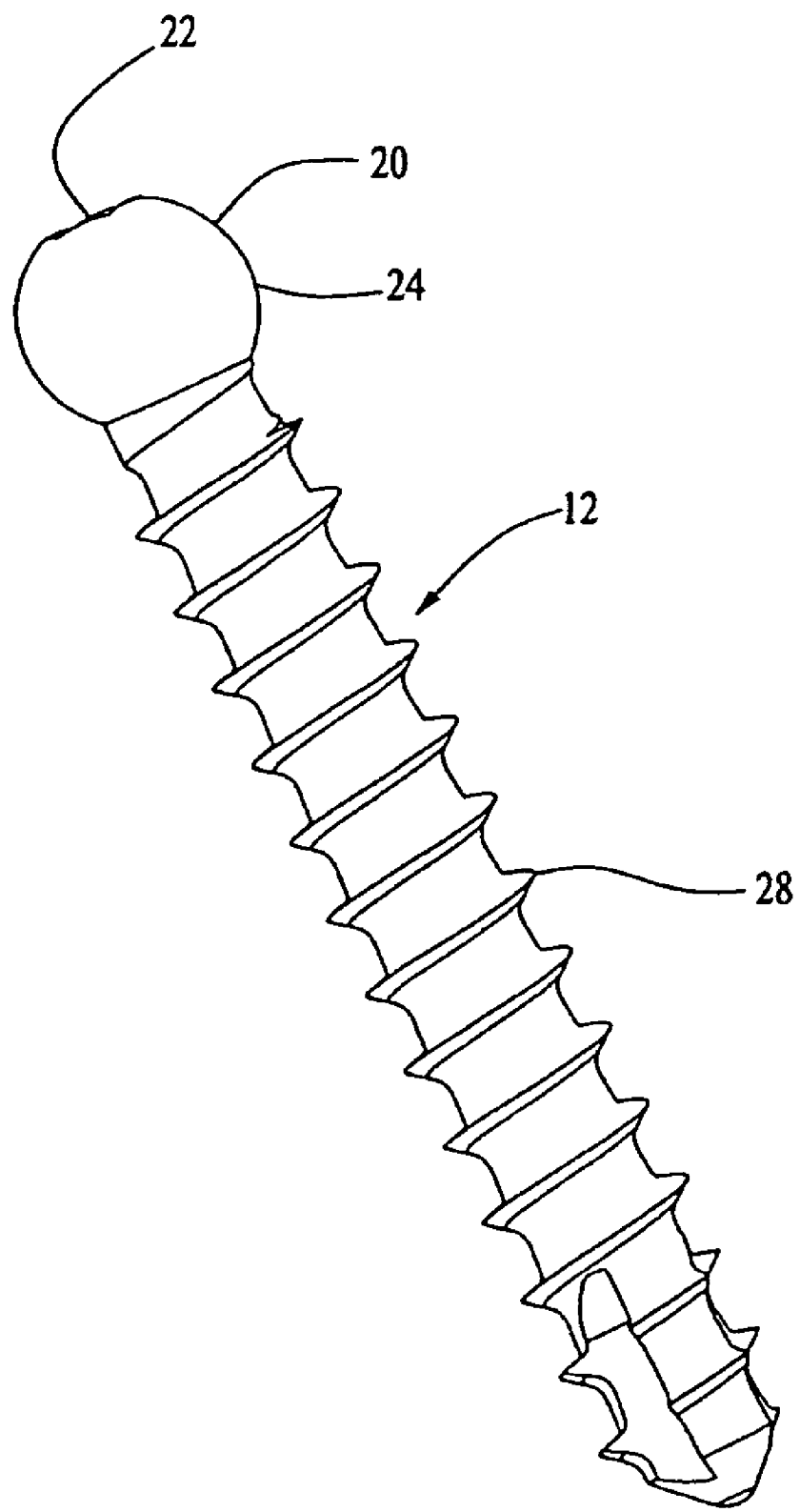
FIG. 2 is a perspective view of the bone screw portion of the assembly of the present invention.

Referring now in detail to the drawings, the variable angle spinal screw assembly 10 of the present invention comprises a pedicle screw 12, a body member 14, a bushing 16 and a locking cap 18. The assembly 10 is used with at least one other such assembly and a stabilization or fixation rod 19 to connect the assemblies and stabilize the vertebras into which the assemblies are inserted. The pedicle screw 12 preferably employed in assembly 10 has a spherical head 20 defining a slot 22 therein used to drive the screw into the bone. The rounded surface 24 defined by the lower portion of screw head 20 rests upon and mates with a rounded interior surface 26 formed in the inner or lower end of the body member 14 of the assembly 10 so as to form a modified ball joint that provides the desired variable angular movement of the body member with respect to the embedded pedicle screw. The threaded shaft portion 28 of screw 12 extends therefrom through the opening 30 in the lower end of body member 14.

The body member 14 of assembly 10 further defines a pair of opposed parallel slots 32 axially disposed in the side wall 34 thereof, which terminate at their lower ends in curvilinear surfaces 36. The two slots 32 are sized to receive the fixation rod therein as shown in the drawings with the walls 35 defining the slots preferably extending upwardly beyond the midpoint of the rod and can be inclined slightly to provide a slight holding force on the rod prior to securing the rod with the locking cap 18. Thus, during assembly, the surgeon exerts a slight downward force on the rod, snapping the rod into the transverse channel defined by the aligned slots 32.

The outer or upper interior surface of side walls 34 of the body member 14 both have radially projecting serrations formed therein defining a plurality of axially aligned ratchet teeth 38. The exterior bottom surface 40 of body member 14 has spaced outwardly extending concave surface 42 formed therein and a pair of perpendicularly disposed concave surfaces 44. Surfaces 42 and 44, together with mating surfaces 24 and 26 on the screw head and body member of the assembly, provide an extended range of motion of the body member 14 with respect to the pedicle screw 12. In one embodiment, the range of motion is about .+−.30.degree. in all directions (as measured from the longitudinal axis of the screw) and about .+−.40.degree. in the inferior-superior direction, the outwardly (as viewed from the screw head) concave surfaces provide the .+−.40.degree. range of motion, for a total motion range of 80.degree. This extended range of motion, as compared to the prior art, allows the surgeon additional freedom in locating the screws and eases the assembly process by reducing the requirement for a rod contouring.

Figure 3A:
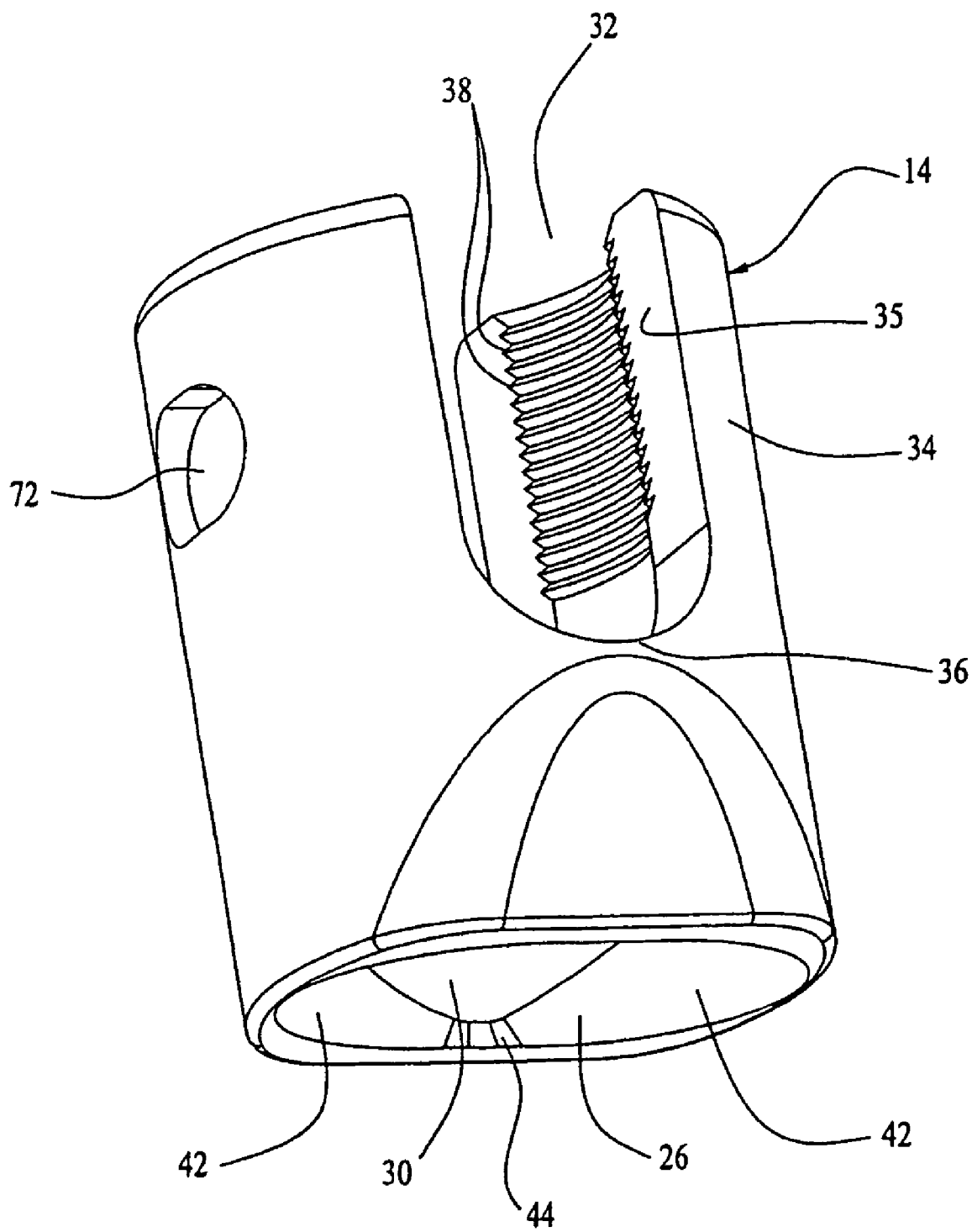
FIGS. 3A and 3B are perspective views of the body member of the assembly of the present invention.
Figure 3B:
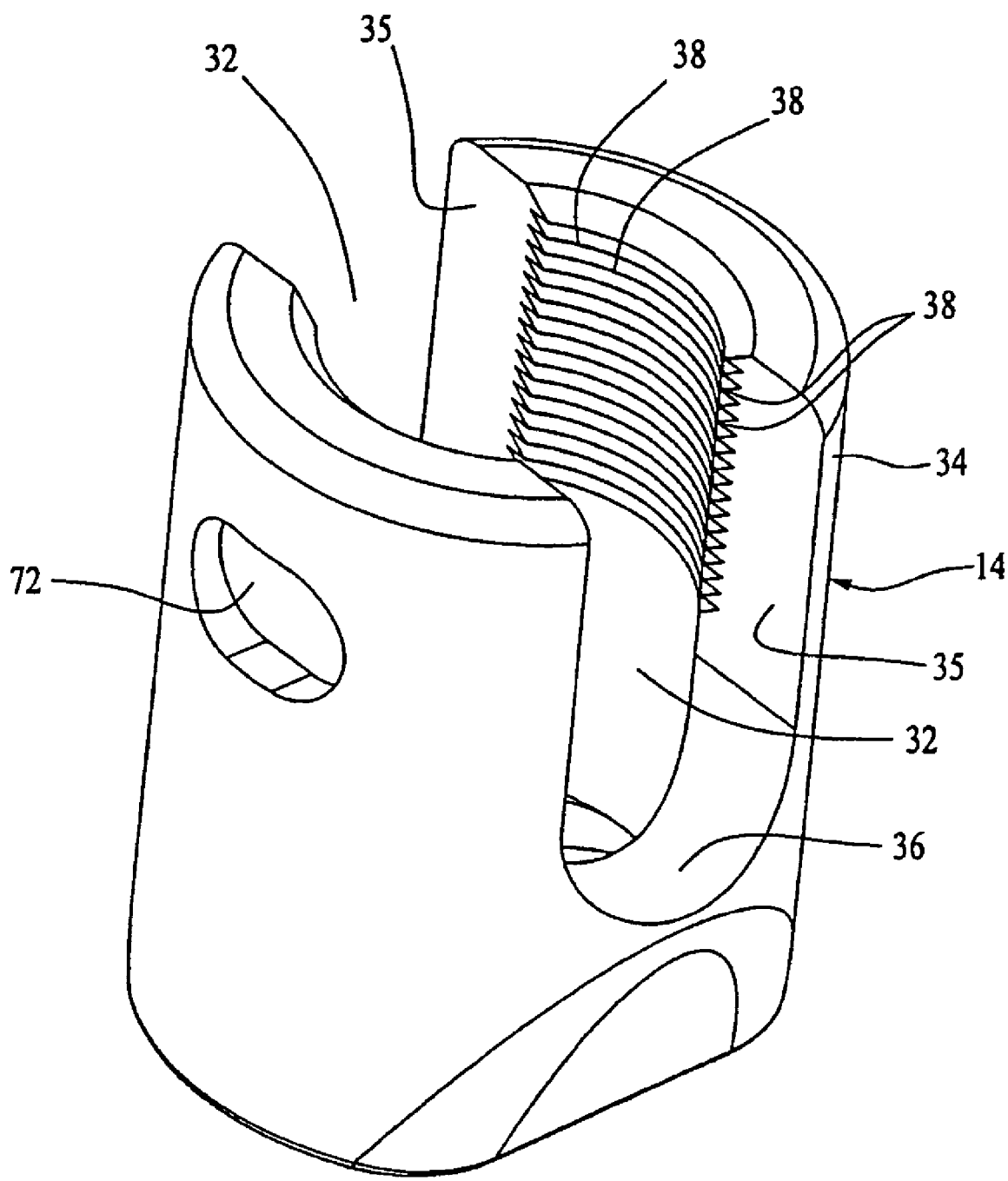
Figure 4:
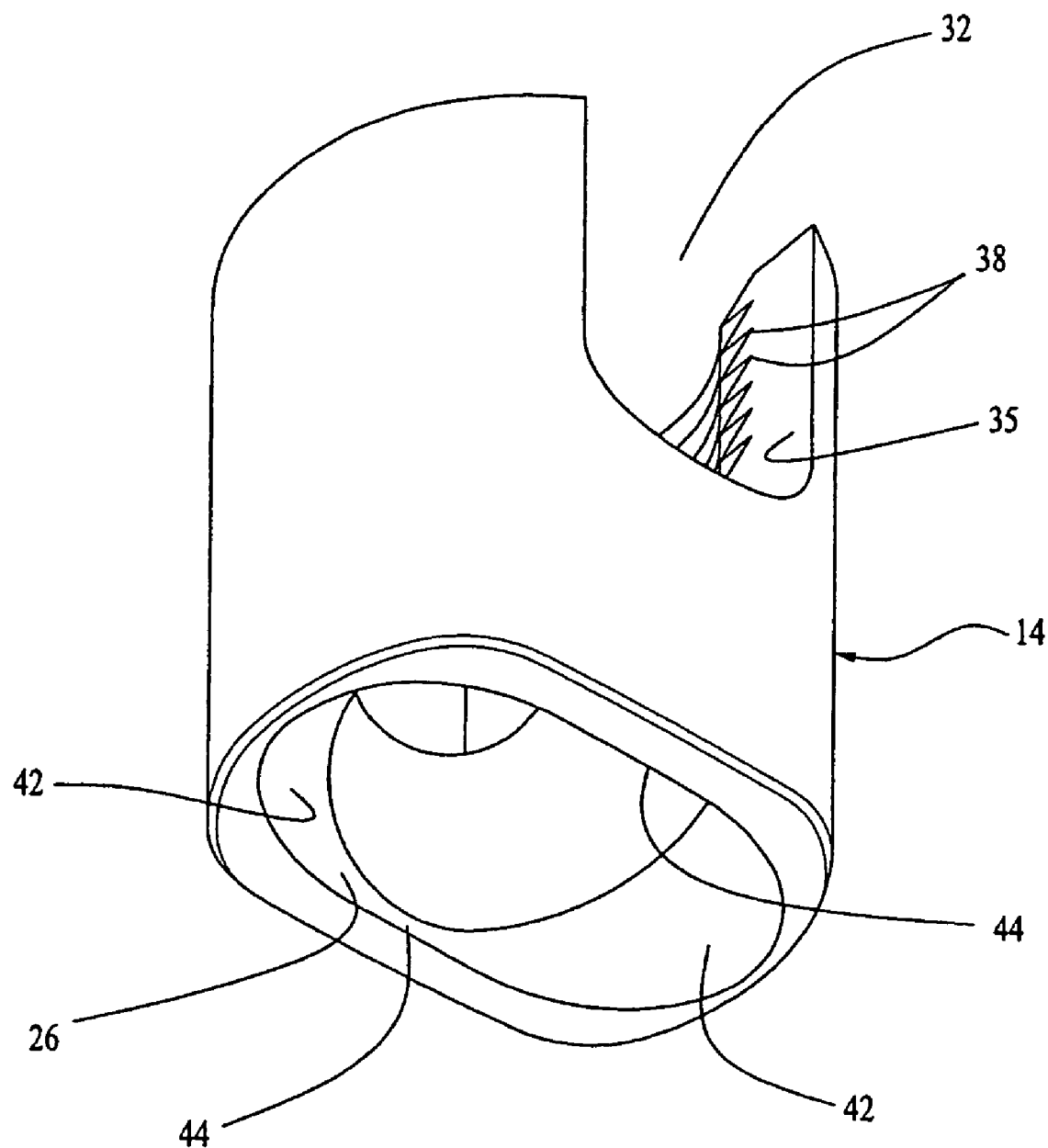
FIG. 4 is another perspective view of the body member of the present invention showing the lower surface thereof.
Figure 5:
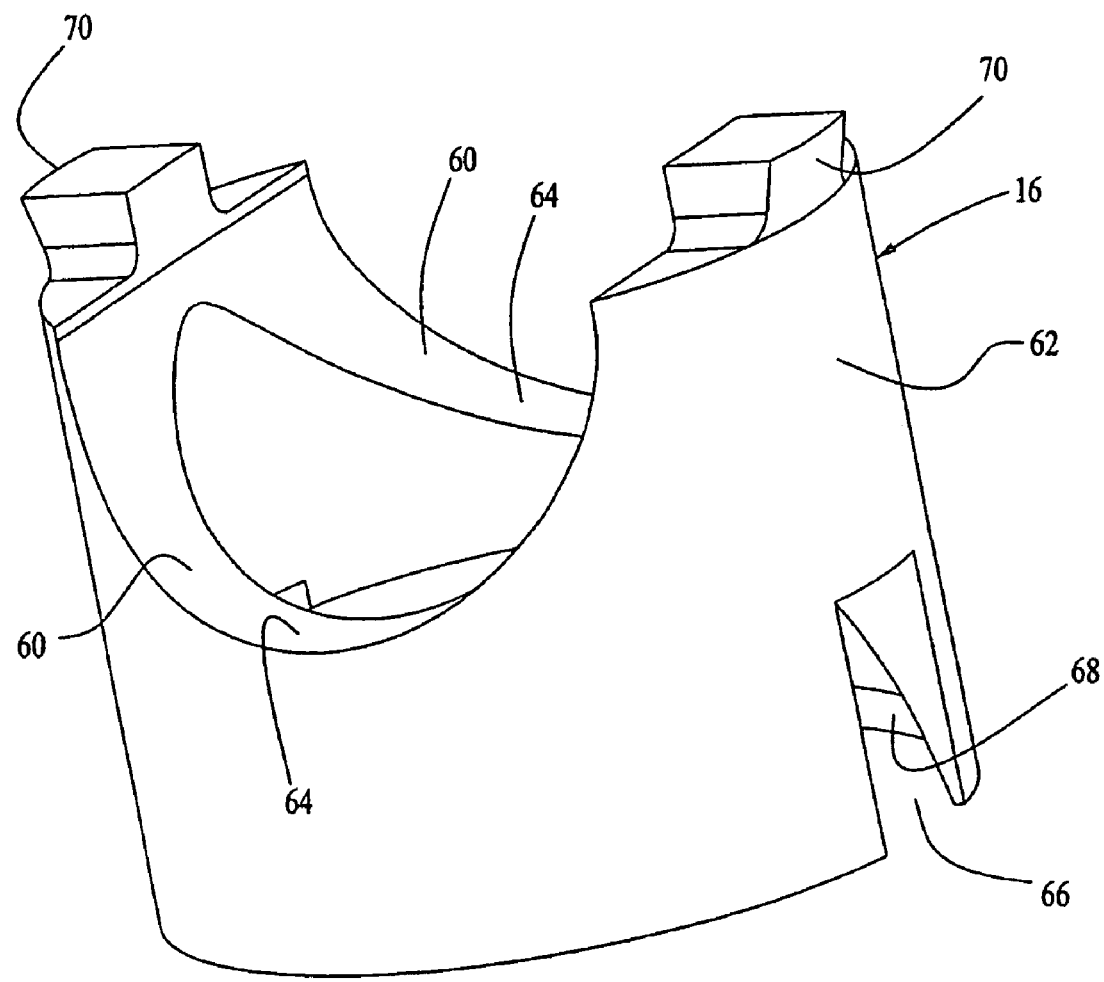
FIG. 5 is a perspective view of the bushing employed in the present invention.
Figure 6A:
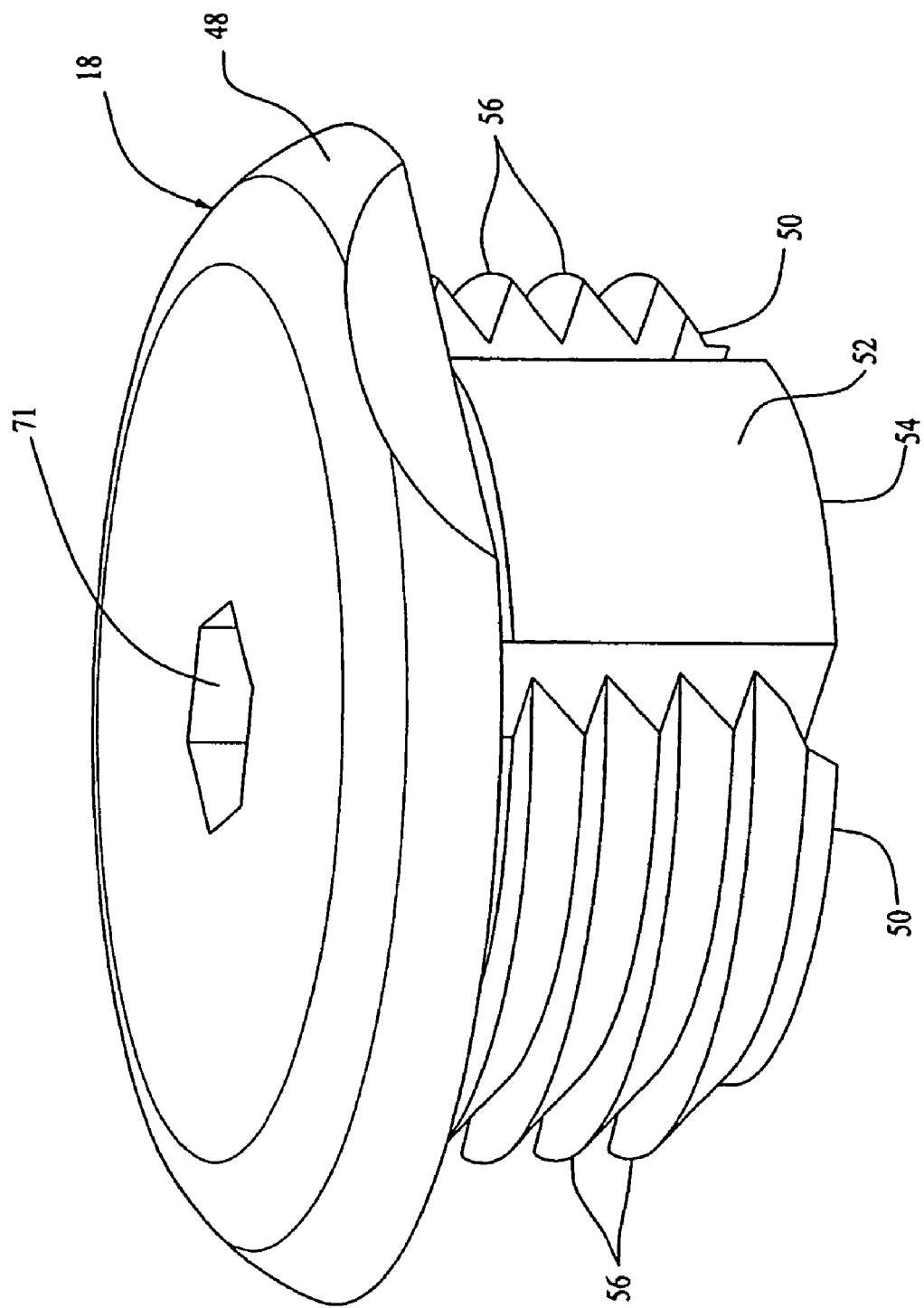

To secure the fixation rod 19 within the body member 14 of the assembly, locking cap 18 is provided. Cap 18 defines a top portion 48, a pair of opposed arcuate depending leg portions 50 and a centrally disposed depending projection 52 equidistantly spaced from leg portions 50. Central projection 52 preferably defines a planar lower or bottom surface 54. The leg portions 50 of cap 18 each have a plurality of radially projecting serrations formed therein that define a plurality of axially aligned ratchet teeth 56 adopted to engage teeth 38 on the opposed interior side walls 34 of the body member 14, as will be described A bushing 16 is preferably employed within the body member 14 of the assembly 10 adjacent side walls 34 to better distribute the longitudinal forces exerted on the pedicle screw. Bushing 16 defines a pair of opposed concave surfaces 60 formed in the upper end of a circular skirt 62 so as to define a seat 64 for the fixation rod 19. The lower portion of bushing skirt 62 is slotted at 66 to provide flexibility therein and defines depending tapered end surfaces 68 adapted to abut opposed sides of the rounded screw head 20. A pair of outwardly projecting opposed resilient tabs 70 are provided at the upper ends of the bushing 16 between concave surfaces 60 that in some embodiments are adapted to be received in a snap fitment within a pair of opposed apertures (not shown) formed in the side wall 34 of body member 14 whereupon the rod seat 64 in bushing 16 is aligned with the channel in the body member. Note that in the illustrated embodiment shown in FIG. 3B, for example, the resilient tabs 70 will engage with the body member 14 inner cylindrical surface located below the ratchet teeth 38, the illustrated aperture 72 being located in the vicinity of the ratchet teeth 38 that cooperate with the locking cap 18 and thus at a distance from the bushing 16. Note that only one of apertures 72 is illustrated in FIGS. 3A and 3B to better illustrate the configuration of the ratchet teeth 38. In an alternative embodiment, the tabs could be removed from the bushing 16 and located on the body member 14 for engagement with apertures or other receiving structure or members formed in opposed sides of the bushing.

To provide a basic stability to the system during initial assembly, the bushing 16 with its slotted lower skirt portion can be configured to provide a press fitment about the screw head 20 so that the pedicle screw 12, body member 14 and bushing 16 will not move freely prior to the insertion and securement of the fixation rod. In addition, the upper portion of the bushing could be configured such that the wall surfaces 60 defining the rod seat 64 therein extend upwardly past the midpoint of the rod and are slightly inwardly inclined. This would provide the same slight holding force when the rod is pushed into the bushing seat 64 that was above described with reference to the channel walls 35 in the body member 14 of the assembly 10.

Upon securing the bushing 16 in the body member 14 and the fixation rod 12 in bushing seat 64, the locking cap 18 is positioned such that the depending leg portions 50 thereon are aligned with the side walls 34 of body member 14. Upon pressing the cap 18 downwardly into body member 14, the ratchet teeth 38 and 56 on the assembly body and cap interlock so as to allow the cap to be pressed downwardly but not retracted. As cap 18 is pressed downwardly into the body member of the assembly, the planar bottom surface 54 of the central projection 52 thereon abuts the fixation rod 19 and presses the rod into and against the seat 64 formed on the upper end of bushing 16. The resulting pressure on the bushing causes the tapered surfaces 68 on the lower end of the bushing to press against the rounded surface of the screw head 20, thereby securing the rod in seat 64 and providing a decentralized and evenly distributed force acting along the longitudinal axis of the screw. Thus, the use of bushing 16 creates a taper lock between the pedicle screw and body member and increases the area of contact therebetween. The result is an improved locking securement over that provided by the earlier described direct contact of the fixation rod against the upper end of the screw head.

The interlocked ratchet teeth will allow the surgeon to tighten the clamping force on the fixation rod by simply pressing downwardly on the locking cap 18. The teeth will hold the component parts in place. To adjust or remove the rod 19, the locking cap 18 is simply rotated 90 degrees about its longitudinal axis, whereupon the teeth 38 on the depending leg portions 50 of the cap are aligned with the open slots 32 in the body member 14, allowing the cap to be simply pulled upwardly away from the fixation rod 19. A hexagonally configured slot 71 is provided in the top portion 48 of cap 18 to facilitate the rotation of the locking cap with a suitably sized mating tool.

In use, at least two of the pedicle screws 12 with the body members 14 and attached bushings 16 disposed about the screw are inserted into the vertebra pedicles spanning the vertebra to be fixated. The surgeon preliminary contours the fixation rod and checks the alignment between the rod and the mating channels formed by the slots in the bushing and body member of the assemblies. Since additional contouring is usually required to improve the alignment, the surgeon incrementally adjusts the rod shape and checks the fit within the channels until the rod properly fits in all channels. During the contouring process, a locking cap 18 can be mated with one or more of the body member 14 (by pressing the cap axially into the body member to create the interlock between the ratchet teeth on the body member and the cap) to temporarily hold the rod in place, thereby assisting the surgeon in achieving an accurate fit. The locking caps are then easily removable (by rotating the cap a quarter of a turn to disengage the interlocking teeth), allowing the rod to be further contoured. Once properly contoured, the rod is inserted into the channels and a locking cap is pressed tightly into each body member and bushing to secure the rod in place. To effect securement of the rod at each of the pedicle screw assemblies, it is solely necessary to press the locking cap longitudinally into the body member such that the bottom surface 54 of the central projection 52 on the cap presses against the fixation rod 19, causing the rod to press downwardly against the bushing 16, which in turn mates with and presses against the head of the pedicle screw.

Figure 10:
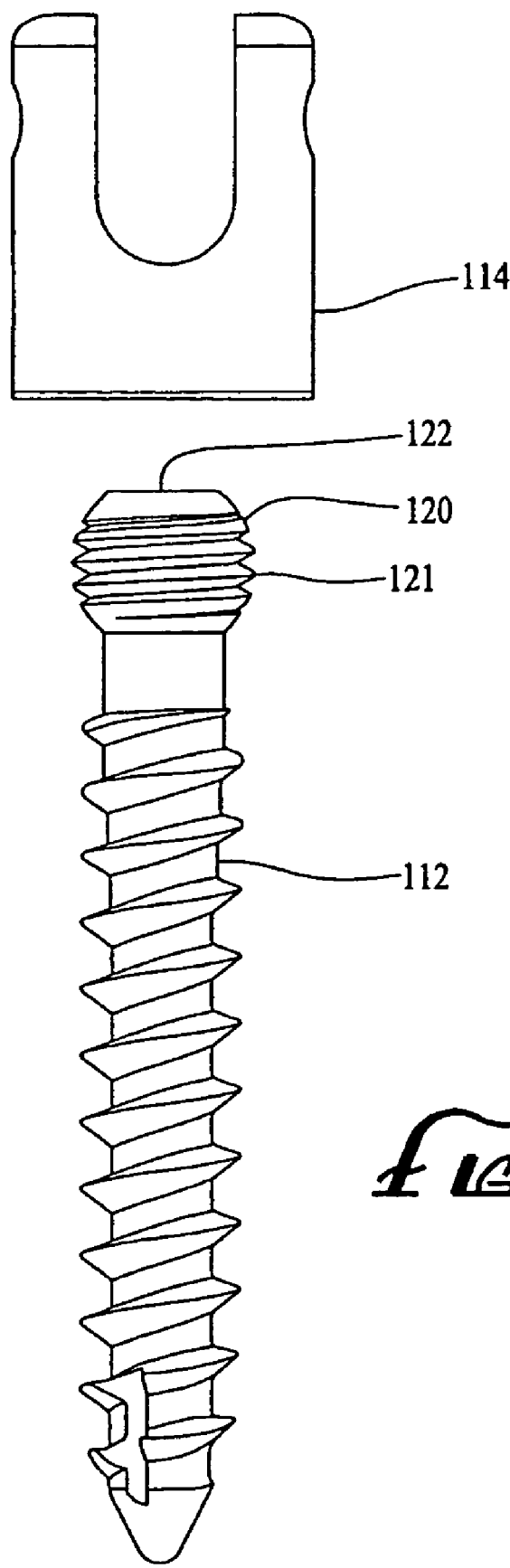
FIG. 10 is an exploded view of a modified form of the pedicle screw and body member employed in the present invention.
Figure 11:
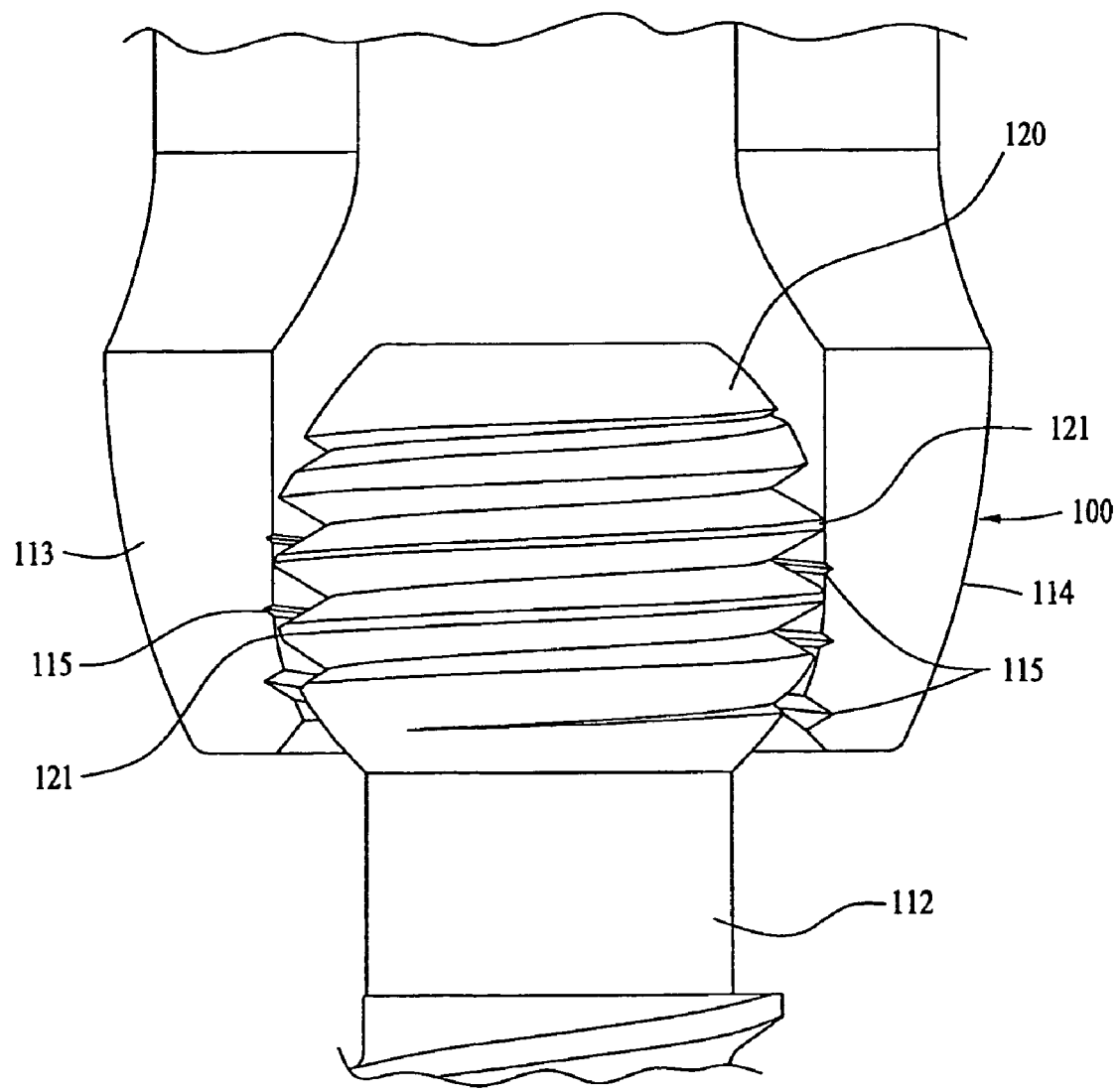
FIG. 11 is a perspective view of the modified pedicle screw and body member of FIG. 10 shown in the attached position prior to threading the body member over the screw head to form the mating relationship between the spherical lower portion of the screw head and the interior lower surface of the body member.

A modified form of the variable angle spinal screw assembly is illustrated in FIGS. 10 and 11. This modified form of the assembly enables the surgeon to insert the pedicle screw in the bone, by itself, unencumbered by the body member. In the prior embodiment, the pedicle screw 12 must be inserted through the body member 14 before the screw can be driven into the bone. With the body member attached, securement of the screw into the bone can be somewhat difficult. In the modified assembly 100, the outer surface of the spherical head portion 120 of the pedicle screw 112 is provided with threads 121, as seen in FIG. 10. As in the prior embodiment, the upper end of head portion 120 is provided with a vertical slot 122 used to drive the screw into place. The lower interior portion 113 of the body member 114 to be used with the modified pedicle screw 112 is provided with threads 115 adapted to engage threads 121 on the screw. As a result, the body member 114 can be threaded onto (see FIG. 11) and over the head 120 of the screw 112 after the screw is driven into place. With the exception of threads 121 and 115, the pedicle screw 112 and body member 114 are identical in configuration to the screw 12 and body member 14 of the prior embodiment. Thus, after the body member 114 is threaded onto and over the screw head and is disposed within the interior of the lower end of body member 114, as seen in FIG. 11, the variable angular relationship therebetween is formed as in the prior embodiment.

Figure 12:
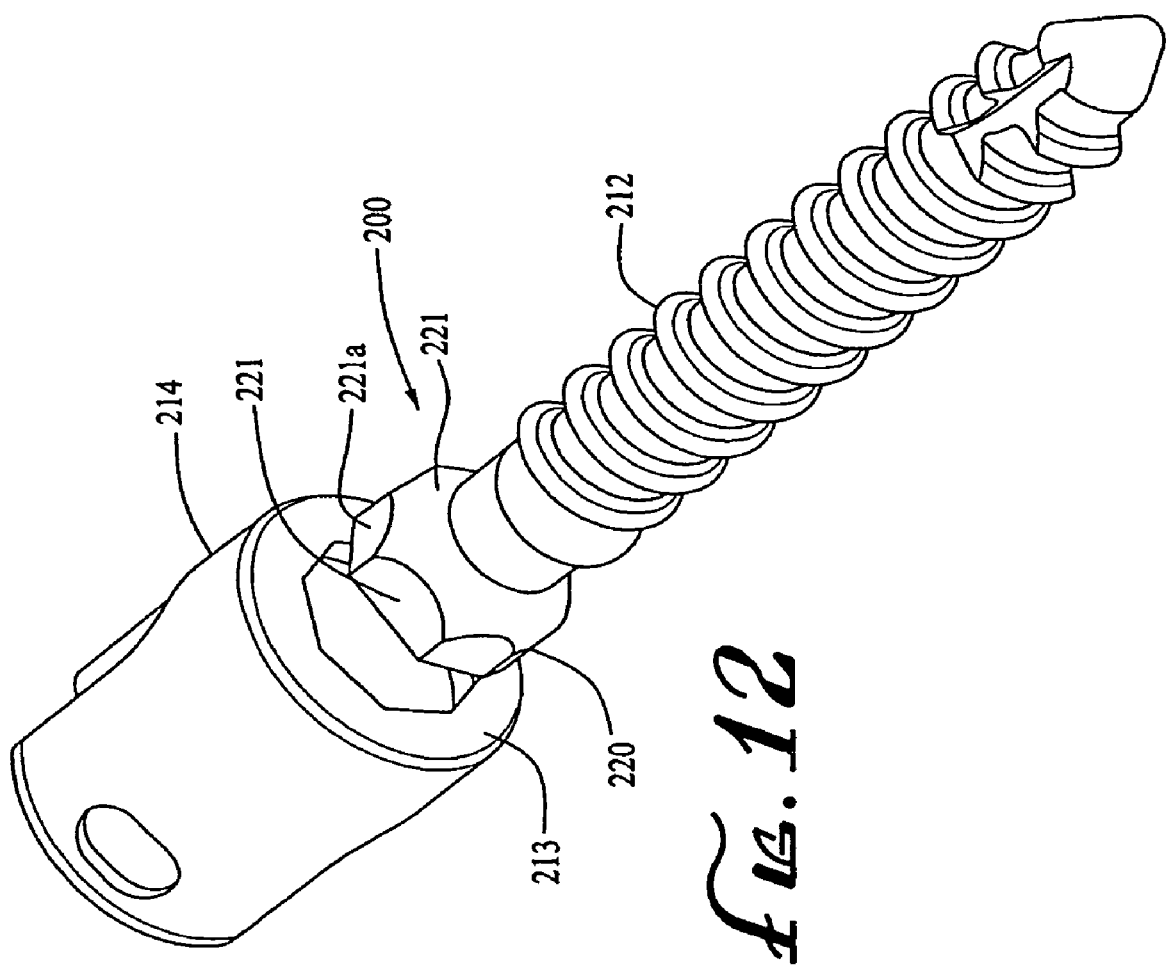
FIG. 12 is an exploded perspective view of another modified form of the pedicle screw and body member employed in the present invention.
Figure 13:
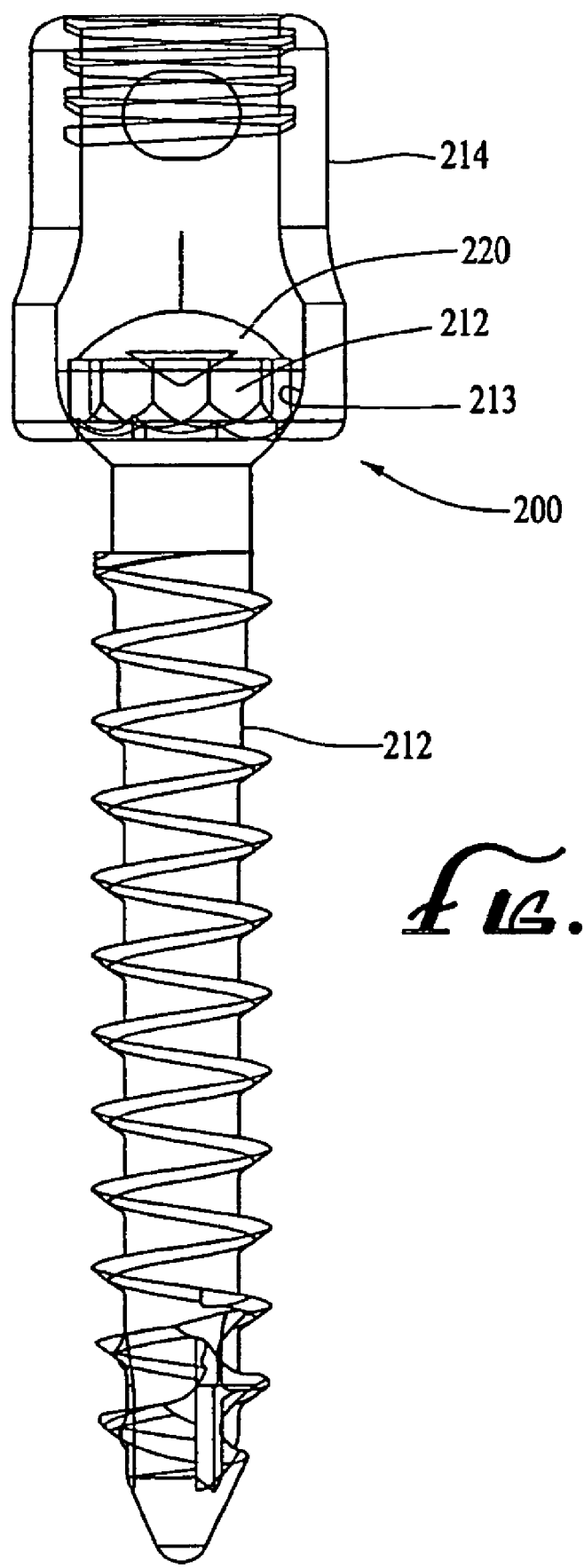
FIG. 13 is a representational side view of the embodiment of the pedicle screw and body member shown in FIG. 12 with the body member on the screw in the mating variable angle position.

A second modified form of the variable angle spinal screw assembly that enables the surgeon to insert the pedicle screw in the bone, by itself, unencumbered by the body member is illustrated in FIGS. 12 and 13. As seen therein, the mating threads on the pedicle screw 112 and body member 114 have been replaced with mating octagonal surfaces. In this second modified assembly 200, the outer surface of the spherical head portion 220 of the screw 212 is provided with an octagonal portion. The octagonal portion is comprised of eight contact surfaces 221, one of which (e.g. 221*a*) is unequal in length to the remaining surfaces. The lower interior portion 213 of the body member 214 to be used with the modified pedicle screw 212 is also provided with an octagonally configured portion adapted to engage and mate with the octagonal surfaces on the screw head. Because of the inclusion of a differently-sized surface on both the screw and body member, the pedicle screw 212 will only align with the body member 214 in only one position, i.e., where the shortened contact surface on the screw head is aligned with the correspondingly shortened surface in the lower interior of the body member. Accordingly, the pedicle screw 212 can again be inserted into the bone without being attached to the body member 214. After the screw 212 is driven into place, the body member 214 can be inserted over the screw head with the octagonal surfaces thereon aligned with the corresponding surfaces on the screw head. By pressing the screw body downwardly, it is completely inserted onto the screw head and the mating octagonal surfaces are moved out of engagement. Upon rotating the body member and pulling upwardly on the body member, such that the head is disposed within the interior of the lower end of body member 214 the variable angular relationship therebetween illustrated in FIG. 13 is formed as in the prior embodiments. It is to be understood that this form of the present invention is not limited to the use of mating octagonal surfaces. Any polygonal configuration could be employed on the screw head and body member wherein at least one of the mating surfaces on the screw head and on the body member is correspondingly off-sized or otherwise differently configured from the remaining surfaces on the screw head and body member.

In another embodiment of the invention, the bushing 16 is not employed. The opposed axial slots 32 in the side wall 34 of the body member of the assembly define a seat for the fixation rod 19. When the locking cap is pressed into the body member with the fixation rod extending thereacross, the planar bottom surface 54 of the central projection 52 again abuts the fixation rod and, in this instance, presses the rod against the upper end of the head of the pedicle screw. For such applications, the body member and pedicle screw would be sized such that the upper surface of the screw would project above the bottom of the seat defined by the axially opposed slots 32 so as to enable the rod to press against the screw and create a rigid, yet adjustable, securement between the body member and the pedicle screw. This embodiment can also be utilized with the modified forms of the pedicle screw 128 and body member 114 shown in FIGS. 10 and 11. In all of these embodiments, the components of the variable angle spinal screw assembly are preferably formed of titanium.

Figure 7:
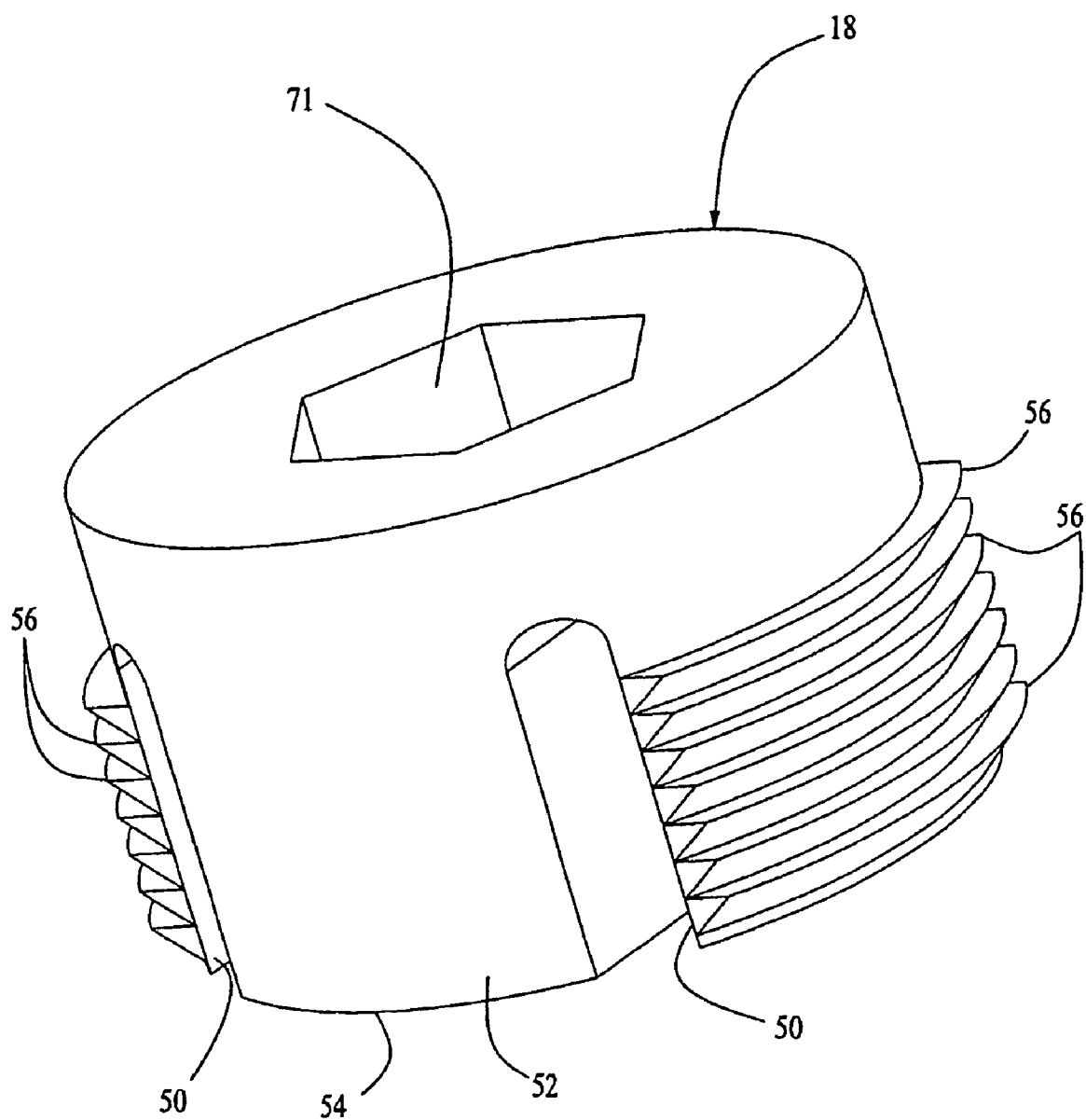
FIG. 7 is a second embodiment of the cap of the present invention.

It should be noted that while the preferred configuration of the locking cap provides a rounded and flush mounting on the upper ends of the body member 14 when the locking cap is fully inserted against the fixation rod, other locking cap configurations could be employed. For example, FIG. 7 illustrates a locking cap having a generally cylindrical perimeter portion in which the ratchet teeth 56 project radially therefrom along leg portions 50. This configuration is illustrated in FIG. 1. As a result, the upper end of the locking cap would be inwardly offset from the upper end of the body member without adversely effecting the operation of the variable angle spinal screw assembly. Various other changes and modifications also could be made in carrying out the present invention.

Although the present invention has been described by way of exemplary embodiments, it should be understood that many changes and substitutions may be made by those skilled in the art without departing from the spirit and the scope of the present invention, which is defined by the appended claims.

What is claimed and desired to be secured by Letters Patent is as follows:

1. A variable angle spinal screw assembly adapted to be secured to a vertebra comprising:
    a) a body member having a lower opening that opens onto an interior surface; the body member including structure adapted to receive a rod in an upper portion thereof;
    b) a screw having a threaded shaft and an upper head portion; the upper head portion being loaded into the body member interior and the shaft extending through the lower opening so as to allow variable angular movement of the screw relative to the body member during assembly;
    c) a bushing located, such that when the head portion is positioned in the body member interior and the rod is received by the body member, the bushing is located between and in contact with the rod and the head portion, the bushing having a seat for receiving the rod, the bushing having a pair of opposed outwardly projecting structures, such that when the bushing is located within the body member interior, the structures engage the body member interior surface and the bushing provides a press fitment about the screw head so that the body member, the screw and the bushing do not move freely prior to securement of the rod; and
    d) a locking structure that when joined with the body member bears against the rod which in turn bears against the bushing that in turn bears against the interior surface of the body member so as to fix the angular position of the body member relative to the screw when in an assembled configuration.

2. The assembly according to claim 1 wherein:
    a) the screw upper portion is uploaded into the body member through the opening.

3. The assembly according to claim 2 wherein:
    a) the body member opening includes a first keyed surface and the screw head portion includes a second keyed surface; the first and second keyed surfaces being sized and shaped to allow passage of screw upper portion though the opening by engagement of and manipulation of the first keyed surface relative to the second keyed surface and thereafter the screw upper portion is received in the body member so that the angle of the pedicle screw can be varied relative to the body member prior to joining of the locking structure with the body member.

4. The assembly according to claim 3 wherein:
a) the first and second keyed surfaces include mating helical wound threads.

5. The assembly according to claim 3 wherein:
a) the first and second keyed surface are shaped to allow passage of the screw upper portion through the opening when in a first alignment and prevent such passage in a second alignment.

6. The assembly according to claim 5 wherein:
a) the first and second keyed surfaces include contact surfaces that are non-identical and that must be aligned in a configuration where identically configured surfaces are matched with one another to allow passage of the upper portion through the opening.

7. The assembly according to claim 1 wherein:
a) the locking structure is a locking cap that is operably secured to the body member above a rod received in the body member and adapted to bear against the rod.

8. A variable angle spinal screw and rod assembly comprising:
a) a body member having an internal region defined by an interior surface and a lower opening that opens onto the body member interior surface; the opening having a first keyed surface;
b) a screw having a lower threaded shaft adapted to implant in a bone and an upper portion; the screw upper portion having a second keyed surface; the first and second keyed surfaces having an aligned configuration and a non aligned configuration; the screw upper portion being uploaded through the opening by manual manipulation when the first and second keyed surfaces are in the alignment configuration; and
c) a bushing positioned in the body member above and in contact with the screw upper portion and in contact with the body member, the bushing being in press fitment about the screw upper portion so that the body member and the bushing do not move freely prior to insertion and securement of the rod.

9. In a spinal screw assembly having a body member and a pedicle screw adapted to be adjusted to various angles of the pedicle screw relative to the body member during assembly and then locked in position with an elongate fixation member; the improvement wherein:
a) the body member has an interior region defined by an interior surface and a lower opening that opens onto the interior surface; the opening having a first keyed surface;
b) the pedicle screw has a lower threaded shank adapted to implant in a bone and an upper portion; the upper portion having a rounded head with an external second keyed surface; and wherein:
c) the first and second keyed surfaces are sized and shaped so as to receive and allow passage of the upper portion through the opening only in an aligned configuration and wherein there is a non-aligned configuration wherein the upper portion cannot pass through the opening such that the pedicle screw upper portion is uploaded through the opening in the aligned configuration and than placed in the non-aligned configuration to allow angular movement of the pedicle screw relative to the body member while securing the pedicle screw upper portion in the body member; and d) further comprising a bushing having an upper elongate fixation member seating surface, an outer surface and a lower skirt, the outer surface being in contact with the interior surface of the body member, the lower skirt abutting opposed sides of the rounded screw head providing a press fitment about the screw head prior to insertion of the elongate fixation member.

10. The improvement of claim 9 wherein the lower skirt is bifurcated.

11. In a variable angle spinal attachment assembly for securing a fixation rod to a vertebra, the assembly having a shank with a threaded body and a substantially spherical head, an outer body member having an upper rod receiving channel communicating with an axial passage and a lower opening through which the threaded body extends, the outer body member further having an interior seating surface forming a polyaxial seat for the shank spherical head, the improvement comprising:
a bushing located within the outer body member, the bushing having an upper rod seating surface, an outer surface in frictional contact with an inner surface of the outer body member, and a lower body portion in frictional contact with the substantially spherical head of the shank, the bushing being in press fitment with the spherical head of the shank body, the bushing and the outer body member being unable to freely move and being in press fitment with respect to one another, wherein some force is required to move the shank into a different angular orientation with respect to the outer body member when the fixation rod is not locked against the bushing.

12. The improvement of claim 11 wherein the shank head is in frictional contact with the interior seating surface.

13. The improvement of claim 11 further comprising first and second opposed resilient tabs extending outwardly from the bushing outer surface.

14. The improvement of claim 13 wherein the resilient tabs press against the inner surface of the body members.

15. The improvement of claim 11 wherein the bushing lower body portion comprises a slotted skirt having tapered end surfaces abutting opposed sides of the spherical head.

16. The improvement of claim 15 wherein the outer surface of the bushing in contact with the inner surface of the body member is at the slotted skirt.

17. The improvement of claim 13 wherein the shank substantially spherical head has a first keyed surface defined by a first thread and the outer body member lower opening is partially defined by a second keyed surface that mates with the first keyed surface to allow passage of the head through the lower opening only in an aligned configuration and wherein there is a non-aligned configuration wherein the head cannot pass through the lower opening such that the head is uploaded through the lower opening in the aligned configuration and than placed in the non-aligned configuration to allow angular movement of the shank relative to the outer body member while securing the shank head in the outer body member.

18. In a variable angle spinal attachment assembly for securing a fixation rod to a vertebra, the assembly having a shank with a threaded body and a rounded head, an outer body member having an upper opening for receiving a rod, the opening communicating with an axial passage further communicating with a lower opening through which the threaded body extends, the outer body member having an interior seating surface forming a polyaxial seat for the shank rounded head, the improvement comprising:

a bushing in press fit engagement with the shank rounded head, the bushing having a body with an upper rod seating surface and a lower skirt, the skirt having slots that define discrete skirt portions depending from the body, the skirt portions having tapered end surfaces configured to abut opposed sides of the rounded screw head, the skirt portions having outer surfaces in contact with the outer body member, the shank, the bushing and the outer body member being unable to move freely with respect to one another, requiring some force to move the shank into a different angular orientation with respect to the outer body member when the fixation rod is not pressing against the bushing rod seating surface.

19. The improvement of claim 18 wherein the shank head is in frictional engagement with the interior seating surface.

20. The improvement of claim 18 wherein the bushing further comprises a pair of outwardly projecting opposed resilient tabs in contact with the outer body member.

21. A polyaxial fixation device comprising:
a) a shank with a spherical head;
b) an outer receiving member for receiving and polyaxially seating the spherical head of the shank, the receiving member having an axial passage formed therein and a rod receiving channel; and
c) a compression bushing disposed within the receiving member and located between and adjacent the shank head and the rod, the bushing having a concave surface adapted to seat at least a portion of the spherical head of the shank and wherein a portion of the bushing has a diameter that is deformable to frictionally engage the spherical head in press fitment and also engage the receiving member when the fixation rod is not pressing against the bushing, with the shank head, the bushing and the receiving member being unable to move freely with respect to one another, requiring some force to move the shank into different angular orientations with respect to the receiving member when the fixation rod is not locked against the bushing.

22. A polyaxial fixation assembly comprising:
a) a shank having a spherical head;
b) an outer receiving member having a first opening for receiving a spinal fixation rod and a second opening having a diameter sized to permit passage of the shank there through while maintaining the spherical head therein, the receiving member further having a spherical seat adjacent the second opening to polyaxially seat the spherical head of the shank; and
c) a compression bushing for frictionally engaging the spherical head to maintain the shank in a desired angular orientation prior to locking with the spinal fixation rod such that a force greater than a frictional engagement force is required to change the angular orientation of the shank with respect to the receiver member, wherein at least a portion of the compression bushing has a diameter that is deformable to frictionally engage the spherical head and the receiver.

23. The assembly of claim 22 wherein the bushing includes end slots defining tapered members around a bottom edge of the bushing.

24. A polyaxial fixation assembly comprising:
a) a shank having a spherical head;
b) an outer receiving member having a first opening for receiving a spinal fixation rod and a second opening having a diameter sized to permit passage of the shank there through while maintaining the spherical head therein, the receiving member further having a spherical seating surface adjacent the second opening to polyaxially seat the spherical head of the shank and an interior surface with a first width; and
c) a compression bushing for frictionally engaging the spherical head to maintain the shank in a desired angular orientation prior to locking with the spinal fixation rod such that a force greater than a frictional engagement force is required to change the angular orientation of the shank with respect to the receiver member, wherein at least a portion of the compression bushing has a second width greater than the first width to provide a press fitment between the bushing and the receiver and a frictional engagement between the spherical head and the receiver.

* * * * *